United States Patent
Helgerson et al.

[11] Patent Number: 6,149,996
[45] Date of Patent: Nov. 21, 2000

[54] MOLDED TIP AND TUBING AND METHOD OF MAKING SAME

[75] Inventors: Jeffrey A Helgerson, Minneapolis; Gary R. Fiedler, Plymouth, both of Minn.

[73] Assignee: Schneider (USA) Inc., Plymouth, Minn.

[21] Appl. No.: 09/007,867

[22] Filed: Jan. 15, 1998

[51] Int. Cl.[7] .............................. A61M 25/00; B32B 1/08; B32B 3/00

[52] U.S. Cl. ..................... 428/36.9; 428/147; 428/157; 428/160; 428/161; 428/170; 428/213; 428/220; 428/423.1; 428/474.4; 604/265; 604/524; 604/525

[58] Field of Search ................ 604/96, 196.17, 604/523, 103, 265, 524, 525; 428/423.1, 474.4, 36.9, 36.91, 141, 147, 148, 156, 157, 161, 160, 163, 167, 168, 170, 173, 174, 212, 213, 220, 223

[56] References Cited

U.S. PATENT DOCUMENTS

| | | | |
|---|---|---|---|
| 4,385,635 | 5/1983 | Ruiz | 128/658 |
| 4,531,943 | 7/1985 | Van Tassel et al. | 604/280 |
| 4,551,292 | 11/1985 | Fletcher et al. | 264/139 |
| 5,009,659 | 4/1991 | Hamlin et al. | 606/159 |
| 5,026,377 | 6/1991 | Burton et al. | 606/108 |
| 5,088,991 | 2/1992 | Weldon | 604/280 |
| 5,240,537 | 8/1993 | Bodicky | 156/244.13 |
| 5,425,712 | 6/1995 | Goodin | 604/96 |
| 5,484,444 | 1/1996 | Braunschweiler et al. | 606/108 |
| 5,509,910 | 4/1996 | Lunn | 604/282 |
| 5,591,172 | 1/1997 | Bachmann et al. | 606/108 |
| 5,628,755 | 5/1997 | Heller et al. | 606/108 |
| 5,653,684 | 8/1997 | Laptewicz et al. | 604/22 |
| 5,662,703 | 9/1997 | Yurek et al. | 623/1 |
| 5,891,110 | 4/1999 | Larson et al. | 604/280 |

OTHER PUBLICATIONS

PEBA Polyether Block Amide, Atochem, Dec. 1987.
Wallstent® Esophageal II Endoprosthesis brochure (481765–0197) received by Schneider (USA) Inc from printing company on Jan. 16, 1997 and provided to National Sales Force the week of Jan. 27, 1997; and A commercially available stent delivery device (Esophageal II) sold by Schneider (USA) Inc has tubing including an inner and outer jacket made of materials including polyurethane 55D (Pellethane 55D), Barium Sulfate, Titanium Dioxide, Carbon Black, and Isoplast 2510, and has an intermediate wire braid layer. A tip is molded on the end of the tubing The molded tip is made of Tecoflex which is a polyether–based thermoplastic, aliphatic polyurethane. The tip and tubing are radiopaque. The Esophageal II device is about 18 French size.

*Primary Examiner*—Ellis Robinson
*Assistant Examiner*—John J. Figueroa
*Attorney, Agent, or Firm*—Todd P. Messal

[57] ABSTRACT

The invention relates to a molded tip on tubing and a method of making the same. The molded tip is molded on the tubing in a mold cavity and is for use in a stent delivery device, guide catheter, or angiographic catheter.

18 Claims, 1 Drawing Sheet

MOLDED TIP AND TUBING AND METHOD OF MAKING SAME

BACKGROUND OF THE INVENTION

The present invention relates generally to a molded tip on tubing and a method of making the same, and more particularly to a molded tip made of polyether block amide such as PEBAX or a thermoplastic polyurethane elastomer such as PELLETHANE on tubing made of a polyetheretherketone such as PEEK for use in a stent delivery device, guide catheter, or angiographic catheter.

A stent delivery device, guide catheter, or angiographic catheter is used in various medical procedures to deliver a prosthesis or treatment to a body vessel. Such devices require superior mechanical characteristics because they are often pushed a significant distance from the body access site to the treatment site.

Angiographic catheters are disclosed for instance in U.S. Pat. Nos. 4,385,635 and 5,088,991. A fiber tip atherectomy catheter is disclosed in U.S. Pat. No. 5,009,659. Catheters with a soft tip are disclosed in U.S. Pat. Nos. 4,531,943 and 5,425,712. Methods of making a catheter with a soft tip are disclosed in U.S. Pat. Nos. 4,551,292 and 5,240,537. A catheter with an expandable wire mesh tip is disclosed in U.S. Pat. No. 5,653,684. Various stent delivery devices are disclosed in U.S. Pat. Nos. 5,026,377; 5,484,444; 5,591,172; 5,628,755; and 5,662,703. Such catheters and devices are used within body vessels of humans for treatment of a variety of conditions.

All references cited herein, including the foregoing, are incorporated herein in their entireties for all purposes.

SUMMARY OF THE INVENTION

The invention relates to a molded tip on tubing assembly and a method of making the same for use in a stent delivery device, guide catheter, or angiographic catheter. The molded tip on tubing advantageously provides an alternative to using an adhesive to bond the tip and tubing.

A benefit of the invention is that the tip and tubing assembly generally provides a superior mechanical bond as compared to an adhesively bonded tip that has been through a UV cure cycle. Generally, the present invention advantageously provides a secure and strong assembly.

The molded tip is formed on the tubing in a mold made of steel or aluminum. The mold may have single or multi-cavities and is designed to accept a portion of the interior tube and provide a seal around any perimeter openings. The mold is closed around the interior tube and placed into the injection molding machine. Resin is injected into the cavity which forms a molded tip around a portion of the tube. Standard injection molding equipment and machinery may be used to make the present invention.

Treatment of a portion of the tube under where the molded tip is formed generally enhances the bond between the molded tip and tube. For example, mechanical or chemical treatment may be performed on the distal portion of the tubing. In addition, a protruding member or surface irregularities of varying size and dimension may be incorporated into the tubing. Treatment may include forming a rolled over tubing surface, adding an attached member, or providing a roughened surface, ridges, notches, grooves, or holes in the tubing to improve the bond strength between the molded tip and tubing.

A preferred treatment includes rolling over the distal end of the interior tube by pushing the tube onto a heated forming pin and against a stop. When the end of the tube hits the stop it rolls back on itself forming a radially extending member. Heating the tool facilitates the forming of the member. When the molded tip is formed around the tubing and member a mechanical lock occurs between the tip and tube upon completion of the molding process and cooling of the assembly to about room temperature. Overall, the member advantageously improves the mechanical bond between the tip and the tube.

PEEK which has a high temperature semi-crystalline structure and is a preferred material for the tubing due to it's high temperature and strength properties. Molding temperatures for forming molded tips are typically up to about 450° F. and PEEK can withstand about 480° F. without any significant degradation in properties. Other materials may also be used provided they have superior mechanical and chemical resistance properties, and are capable of surviving molding temperature without degradation.

The desired molded tip material is generally easily molded and is flexible when cured. The two preferred materials for the molded tip are PELLETHANE 90A, a polyurethane material with a Shore hardness of 90A, and PEBAX 3533, a polyether block amide with a Shore hardness of 35D. Molded tip materials having a flexural modulus of about 2,800 to about 10,000 psi are also preferred. Properties of several grades of PEBAX are disclosed in Atochem's brochure entitled "PEBAX Polyether Block Amide" (Dec. 1987).

In sum, the invention relates to a molded tip on tubing. The tubing is made of one or more materials and includes a proximal end, a distal end, a distal portion, a longitudinal axis, and an outside surface. The distal portion has a first melting temperature. The molded tip includes an outside surface forming a predetermined shape and proximal and distal ends. The molded tip is made of a thermoplastic or polymeric material having a second melting temperature less than the first melting temperature of the distal portion of the tubing disposed under the molded tip. The molded tip is disposed on the distal end of the tubing, substantially surrounds the tubing and treated portion, extends proximal and distal of the distal end of the tubing to form a tubing and molded tip assembly, and provides a mechanical bond therebetween. The melting temperature of the distal portion of the tubing may be greater than about 300° F. and the melting temperature of the molded tip may be less than about 625° F. The treated portion may include one or more members extending in an outward radial direction from the tubing as measured from the longitudinal axis of the tubing to provide one or more structural surfaces for the molded tip to be disposed thereabout. The molded tip may have a flexural modulus ranging from about 2,800 psi to about 10,000 psi. The molded tip may have a Shore hardness ranging from about 70A to about 11 0A or about 20D to about 50D. The molded tip may be made of a polyurethane material with a Shore hardness of about 90A or a polyether block amide with a Shore hardness of about 35D. The molded tip may be made of PELLETHANE 90A or PEBAX 3533. The tubing may be made of polyether block amide. The mechanical bond may withstand a tensile force of at least 6 pounds. At least a portion of the outside surface at the distal end of the tubing may have a substantially coarse or roughened surface and provides irregularities for enhanced mechanical bonding between the tubing and molded tip. The tubing may have one or more lumens. The assembly may be used in a stent delivery device, guide catheter, or angiographic catheter. The molded tip may be formed on the tubing at a temperature of about 275° F. to about 500° F. The molded tip may be made from a material which is melted prior to being disposed in a mold assembly. The molded tip may be substantially flexible.

The invention also relates to a method of forming a tip on tubing including providing tubing having one or more melting temperatures, a proximal and distal end, and a treated outside surface portion having one or more irregularities; providing a mold having a cavity with a predetermined shape, the mold adapted to support a portion of the tubing, and the cavity adapted to contain thermoplastic or polymeric material disposed or injected about the portion of the tubing; disposing at least the distal end of the tubing into the cavity of the mold; and disposing or injecting thermoplastic or polymeric material, at a temperature less than the melting temperature of the portion of the tubing in or about the vicinity of the mold, about the outside surface of the distal portion of the tubing, the thermoplastic or polymeric material extending at least proximal of the distal end of the tubing to form a molded tip and tubing assembly. The method may further include providing surface treatment of the distal portion of the tubing; cooling the tip and tube assembly and mold, and removing the tip and tube assembly from the mold; or sealing the mold. The method may include heating the thermoplastic or polymeric material to a temperature greater than about 275° F. and less than about 500° F.

The invention also relates to a molded tip and tubing assembly made by the process including providing tubing having one or more melting temperatures, proximal and a distal ends, and an outside surface; providing a mold having a cavity with a predetermined shape, the mold adapted to support the distal end of the tubing and contain thermoplastic or polymeric material disposed about the distal end of the tubing; disposing the distal end of the tubing into the mold; disposing or injecting thermoplastic or polymeric material, at a temperature less than the melting temperature of the distal portion of the tubing disposed in the mold, about the outside surface of the distal end of the tubing, the thermoplastic or polymeric material extends proximal and distal of the distal end of the tubing and forms a molded tip and catheter assembly in the mold; cooling the tip and catheter assembly and mold; and removing the tip and catheter assembly from the mold. The tubing may be medical grade tubing. The mold may be made from a metal including steel or aluminum. The molded tip and tubing assembly may be used in an implantable device or medical device.

The invention also relates to a molded tip on tubing assembly. The tubing includes a polyether block amide material, a proximal end, a distal end, a distal portion, a longitudinal axis, an outside surface, and a treated portion including one or more members extending in an outward radial direction from the tubing as measured from the longitudinal axis. The members provide one or more structural surfaces for the molded tip to be disposed thereabout. The distal portion of the tubing has a melting temperature greater than about 275° F. A molded tip includes an outside surface forming a predetermined shape and proximal and distal ends. The molded tip is made of a polyether block amide or a thermoplastic polyurethane elastomer material having a melting temperature less than about 625° F. The molded tip is disposed on the distal end of the tubing, substantially surrounds the tubing and treated portion, and extends at least proximal of the distal end of the tubing to form a tubing and molded tip assembly. The tubing and molded tip assembly is used in at least one of a stent delivery device, guide catheter, or angiographic catheter.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawings and description are to be regarded as illustrative in nature, and not as restrictive.

DETAILED DESCRIPTION OF THE INVENTION

Figure 1:
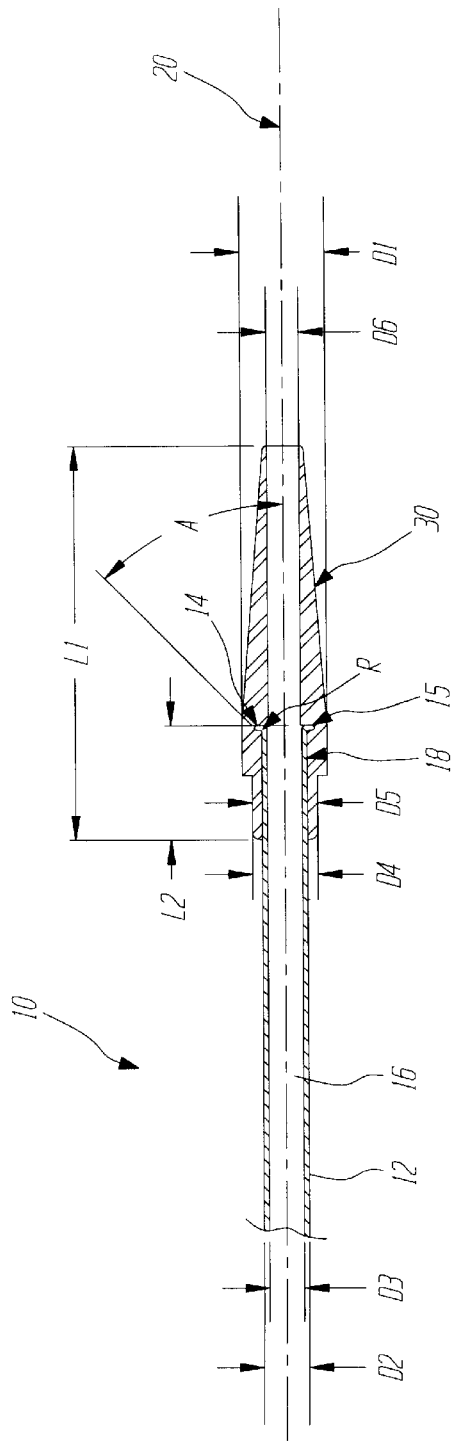
FIG. 1 is a side view of a tip and tubing assembly embodying the present invention.

Reference is made to FIG. 1 illustrating the molded tip 30 disposed on tubing 12 forming an assembly 10. The molded tip 30 on tubing 12 advantageously eliminates adhesives and provides a generally superior mechanical bond between the components 12, 30. The molded tip 30 is formed in a cavity of a mold which supports the distal end 18 of the tubing 12. The molded tip 30 is preferably made of a thermoplastic or polymeric material having a lower melting temperature than the portion of the tubing 12 that is placed in the cavity of the mold. It is envisioned that the tubing 12 may be made of different materials having different melting temperatures, however, the tubing is preferably made of one material. The distal portion 18 of the tubing 12 is placed in the mold and supported by the mold and the liquid molded tip material is injected or disposed into the cavity. When the liquid molded tip cools to a solid molded tip material, the tubing and tip assembly 10 is removed from the mold. The cavity has a preformed shape slightly larger than the desired molded tip 30 in order to account for shrinkage and for removal of the tip 30 from the mold.

A preferred shape of the molded tip 30 on tubing 12 is illustrated in FIG. 1, although any number of mold shapes may be used to form the molded tip and tubing assembly 10. The molded tip and tubing assembly 10 may be used in delivery devices and catheters ranging in size from about 3 French to about 34 French, although, smaller and larger sizes are also envisioned. The length of the tubing 12 can be most any length depending on the treatment and use. Table 1 below describes preferred ranges of dimensions for about 3 French to about 14 French size devices incorporating the molded tip on tubing assembly 10. Devices outside the ranges described are also envisioned.

TABLE 1

| Dimension | Range |
| --- | --- |
| D1 | 1 mm to 4.7 mm |
| D2 | .51 mm to 1.32 mm |
| D3 | .25 mm to .99 mm |
| D4 | .81 mm to 4.22 mm |
| D5 | .78 mm to 4.31 mm |
| D6 | .25 mm to .99 mm |
| L1 | 3 mm to 5 mm |

TABLE 1-continued

| Dimension | Range |
| --- | --- |
| L2 | 3 mm to 5 mm |
| L3 | 3 mm to 5 mm |
| Radius R | .25 mm to .30 mm |
| Angle A | 0 degrees to 210 degrees |

The tubing 12 at the distal portion 18 may have a member 14 which is flared in a radially outward direction to provide a locking mechanism in the molded tip 30 to prevent longitudinal movement of molded tip 30 off the tubing 12. The angle A of the member 14 extending from the longitudinal axis 20 of the tubing 12 may range from about 0° to about 210° measured from the longitudinal axis of the tubing, and is preferably in the range of about 45° to about 135°. The length of the surface treatment L3 is preferably at least the length of L2 corresponding to the amount of tubing disposed under the molded tip 30. The member 14 or distal end 15 of the tubing 12 is positioned at a predetermined longitudinal position in the molded tip 30. The tubing 12 and molded tip 30 may have a lumen 16 extending therethrough. The molded tip 30 may have an equal, larger, or smaller size diameter lumen 16 than the lumen 16 of the tubing 12.

Figure 2:
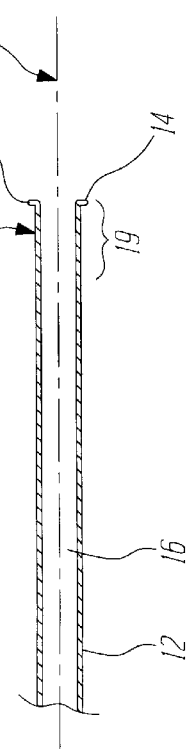
FIG. 2 is a cross-section of the tubing with a protruding member.

FIG. 2 illustrates a cross-section of the tubing 12 with a protruding roll over member 14 at the distal portion 18. The tubing 12 preferably has surface treatment 19 over a portion L3 to be disposed under the molded tip 30. The surface treatment is further illustrated in FIG. 3 and described in greater detail below. The surface treatment 19 may extend over member 14 as well to promote a stronger mechanical bond.

Figure 3:
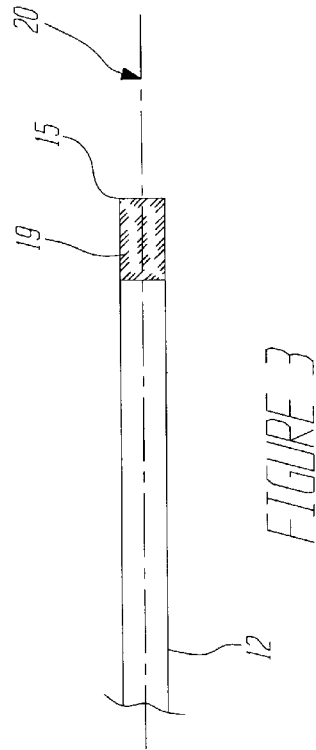
FIG. 3 is a side view of the tubing illustrating without a protruding member and with an area of surface treatment.

FIG. 3 illustrates tubing 12 without a protruding roll over member 14 and illustrates surface treatment 19 over a portion L3 on the outside surface at the distal portion 18. In addition to providing a rollover member 14, surface treatment 19 may further include providing a coarse surface, an attached member, ridges, notches, grooves, or holes for generally greater surface area for the liquid resin material to form about for a stronger mechanical bond. Excluding the rollover member 14 or an attached member, surface irregularities measured from an untreated surface are generally no larger in size than the thickness of the wall of the tubing. Preferably, surface irregularities (peaks and valleys) such as knurling and surface texture are no greater than a maximum of about 10% of the tubing 12 wall thickness. Holes may penetrate the tubing wall and exceed this maximum 10% percentage. Knurling is impressing a design into the tubing surface. Surface texture is the repetitive or random deviations from the nominal surface (untreated surface) which form the three-dimensional topography of the tubing surface. Surface roughness consists of the finer irregularities of the surface texture generally including those irregularities that result from a production process.

Although the present invention has been described with reference to preferred embodiments, those skilled in the art will recognize that changes can be made in form and detail without departing from the spirit and scope of the invention.

It will be evident from considerations of the foregoing that the molded tip and tubing assembly may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A molded tip and tubing assembly comprising:
   a tubing, having a length and made of one or more materials and including a proximal end, a distal end, a distal portion, a longitudinal axis, and an outside surface, the distal portion of the tubing having a first melting temperature, and a treated surface on the outside surface portion, the treated surface portion having surface irregularities; and
   a molded tip having an outside surface forming a predetermined shape and proximal and distal ends, the molded tip made of a thermoplastic or polymeric material having a second melting temperature less than the first melting temperature of the distal portion of the tubing, the molded tip disposed on the distal end of the tubing, bonded to the treated portion, and substantially surround the tubing and treated portion, and extending proximal and distal of the distal end of the tubing to form a tubing and molded tip assembly.

2. The molded tip and tubing assembly of claim 1 wherein the melting temperature of the distal portion of the tubing is greater than about 300° F. and the melting temperature of the molded tip is less than about 625° F.

3. The molded tip and tubing of claim 1 wherein the surface irregularities are adapted to provide one or more structural surfaces for the molded tip to be disposed thereabout.

4. The molded tip and tubing assembly of claim 1 wherein the tip has a flexural modulus ranging from about 2,800 psi to about 10,000 psi.

5. The molded tip and tubing assembly of claim 1 wherein the tip has a Shore hardness ranging from about 70A to about 110A or about 20D to about 50D.

6. The molded tip and tubing assembly of claim 5 wherein the tip is made of a polyurethane material with a Shore hardness of about 90A or a polyether block amide with a Shore hardness of about 35D.

7. The molded tip and tubing assembly of claim 5 wherein the tip is made of one of polyurethane or polyether block amide.

8. The molded tip and tubing assembly of claim 1 wherein the tubing is made of a polyether block amide.

9. The molded tip and tubing assembly of claim 1 wherein the length of tubing and molded tip are mechanically bonded to each other, and wherein the mechanical bond withstands a tensile force of at least 6 pounds.

10. The molded tip on tubing assembly of claim 1 wherein at least a portion of the outside surface at the distal end of the tubing has a substantially coarse surface adapted to provide additional surface area for mechanical bonding between the tubing and tip.

11. The molded tip and tubing assembly of claim 1 wherein the tubing has one or more lumens.

12. The molded tip on tubing assembly of claim 1 wherein the assembly is used in a stent delivery device, guide catheter, or angiographic catheter.

13. The molded tip and tubing assembly of claim 1 wherein the molded tip is formed on the tubing at a temperature of about 275° F. to about 500° F.

14. The molded tip and tubing assembly of claim 1 wherein the molded tip is made from a material which is melted prior to being disposed in a mold assembly.

15. A molded tip and tubing assembly made by the process comprising:

providing tubing having one or more melting temperatures, a proximal and a distal end, a treated portion at the distal portion to provide one or more surface irregularities on an outside surface;

providing a mold having a cavity with a predetermined shape, the mold adapted to support the tubing and contain a melted material disposed about the distal end of the tubing;

disposing the distal end of the tubing into the mold;

disposing or injecting thermoplastic or polymeric material, at a temperature less than the melting temperature of the distal portion of the tubing disposed in the cavity, about the outside surface of the distal end of the tubing, the thermoplastic or polymeric material extending proximal and distal of the distal end of the tubing and forming a molded tip and catheter assembly in the mold;

cooling the tip and catheter assembly and mold; and removing the tip and catheter assembly from the mold, the tip and catheter assembly adapted to be used in a medical device.

16. The molded tip and tubing assembly made by the process of claim 15 wherein the tubing is medical grade tubing.

17. The molded tip and tubing assembly made by the process of claim 15 wherein the mold is made from a metal including one of steel or aluminum.

18. A molded tip on tubing comprising:

tubing including a polyether block amide material, a proximal end, a distal end, a distal portion, a longitudinal axis, an outside surface, and a treated portion including surface irregularities thereon, the irregularities adapted to provide one or more structural surfaces for the molded tip to be disposed thereabout, the distal portion of the tubing having a melting temperature greater than about 275° F.; and a molded tip including an outside surface forming a predetermined shape and proximal and distal ends, the molded tip made of a polyether block amide or a thermoplastic polyurethane elastomer material having a melting temperature less than about 625° F., the molded tip adapted to be disposed on the distal end of the tubing, substantially surround the tubing and treated portion, bonded to the tubing and extending at least proximal of the distal end of the tubing to form a tubing and molded tip assembly herein the tubing and molded tip assembly is used in at least one of a stent delivery device, guide catheter, or angiographic catheter.

* * * * *